United States Patent [19]

Valencia et al.

[11] Patent Number: 4,511,382
[45] Date of Patent: Apr. 16, 1985

[54] METHOD OF SEPARATING ACID GASES, PARTICULARLY CARBON DIOXIDE, FROM METHANE BY THE ADDITION OF A LIGHT GAS SUCH AS HELIUM

[75] Inventors: Jaime A. Valencia, Sugarland; Robert D. Denton, Houston, both of Tex.

[73] Assignee: Exxon Production Research Co., Houston, Tex.

[21] Appl. No.: 532,343

[22] Filed: Sep. 15, 1983

[51] Int. Cl.³ .............................................. F25J 3/02
[52] U.S. Cl. .......................................... 62/20; 62/28
[58] Field of Search ............... 62/9, 11, 22, 17, 20, 62/27, 28; 55/68, 73

[56] References Cited

U.S. PATENT DOCUMENTS

| | | |
|---|---|---|
| 1,881,115 | 10/1932 | Bottoms . |
| 2,716,332 | 8/1955 | Haynes . |
| 3,239,996 | 3/1966 | Huffman et al. . |
| 3,355,902 | 12/1967 | Crawford et al. . |
| 3,512,368 | 5/1970 | Harper . |
| 3,653,220 | 4/1972 | Foster et al. ........................... 62/22 |
| 3,683,634 | 8/1972 | Streich . |
| 3,724,226 | 4/1973 | Pachaly . |
| 3,740,962 | 6/1973 | Fan . |
| 4,097,250 | 6/1978 | Pagani et al. . |
| 4,149,864 | 4/1979 | Eakman et al. . |
| 4,152,129 | 5/1979 | Trentham et al. . |
| 4,318,723 | 3/1982 | Holmes et al. . |
| 4,370,156 | 1/1983 | Goddin et al. . |

Primary Examiner—Frank Sever
Attorney, Agent, or Firm—E. Thomas Wheelock; H. E. O'Niell

[57] ABSTRACT

A method of separating acid gases, particularly carbon dioxide, from methane by cryogenic distillation. The method includes the step of adding helium to the stream to be separated to increase the critical pressure of the methane-carbon dioxide present. The cryogenic distillation tower may then be operated at a higher pressure and without the formation of solid carbon dioxide.

17 Claims, 5 Drawing Figures

METHANE-CARBON DIOXIDE SYSTEM

METHOD OF SEPARATING ACID GASES, PARTICULARLY CARBON DIOXIDE, FROM METHANE BY THE ADDITION OF A LIGHT GAS SUCH AS HELIUM

FIELD OF THE INVENTION

This invention is a method for effectively separating acid gases, in particular carbon dioxide, from methane-containing gases by the addition of an effective amount of a light gas such as helium to increase the critical pressure of the mixture.

BACKGROUND OF THE INVENTION

In the past few years, the price paid for natural gas used as fuel and a chemical feedstock has been steadily increasing. The desire to sell increasing amounts of natural gas has led, to some extent, to the exploration of new and forbidding areas for additional supplies of gas. However, some newer fields, although quite large, contain gas having only 25% to 40% methane. The remaining 60% to 75% is typically a mixture of acid gases, principally carbon dioxide, but also hydrogen sulfide, carbonyl sulfide, carbon disulfide, and various mercaptans.

Carbon dioxide acts as a diluent and, in the amount noted above, lowers the heat content of the natural gas to the point it may not even burn. The sulfur-bearing compounds are at best noxious and may be lethal. In addition, in the presence of water, these components render the gas very corrosive in nature. Clearly, it is desirable to remove acid gases to produce a sweet and concentrated methane gas having a heating value of near 1,000 BTU/SCF either for delivery to a pipeline or conversion to LNG.

Separation of carbon dioxide from methane is not one made with ease. Consequently, significant work has been applied to the development of methane/carbon dioxide separation methods. The processes can be separated into four general classes; absorption by physical solvents, absorption by chemical solvents, adsorption by solids, and distillation.

Currently, cryogenic distillation is considered one of the most promising methods of separating acid gases, particularly carbon dioxide, from methane. The high relative volatility of methane with respect to carbon dioxide makes such processes theoretically very attractive. However, the methane/carbon dioxide distillative separation has a significant disadvantage in that solid carbon dioxide exists in equilibrium with vapor-liquid mixtures of carbon dioxide and methane at particular conditions of temperature, pressure, and composition. Obviously, the formation of solids in a distillation tower has the potential for plugging the tower and its associated equipment. Increasing the operating pressure of the tower will result in warmer operating temperatures and a consequent increase in the solubility of carbon dioxide, thus narrowing the range of conditions at which solid carbon dioxide forms. However, additional increases in pressure will cause the carbon dioxide-methane mixture to reach and surpass its critical conditions. Upon reaching criticality, the vapor and liquid phases of the mixture are indistinguishable from each other and therefore cannot be separated. A single-tower equilibrium separation operating in the vapor-liquid equilibrium region bounded between carbon dioxide freezeout conditions and the carbon dioxide-methane critical pressure line may produce a product methane stream containing 10% or more carbon dioxide. By comparison, specifications for pipeline quality gas typically call for a maximum of 2%-4% carbon dioxide and specifications for an LNG plant typically require less than 100 ppm of carbon dioxide. Clearly, a distillative separation at the above conditions is unacceptable.

Various methods have been devised to avoid the conditions at which carbon dioxide freezes and yet obtain an acceptable separation. Two processes which utilize additives to aid in the separation are disclosed in U.S. Pat. No. 4,149,864 to Eakman et al, issued Apr. 17, 1979, and U.S. Pat. No. 4,318,723 to Holmes et al, issued Mar. 9, 1982.

Eakman et al discloses a process for separating carbon dioxide from methane in a single distillation column. If insufficient hydrogen is present in the column feedstream, hydrogen is added to provide a concentration from about 6 to 34 mole percent, preferably from about 20 to about 30 mole percent. The separation is said to take place without the formation of solid carbon dioxide. The tower pressure is preferably held between 1025 and 1070 psia.

Holmes et al adds alkanes having a molecular weight higher than methane, preferably butane, to the tower feed to increase the solubility of carbon dioxide and decrease its freezing temperature line. The additive n-butane is added at an amount from about 5 moles to 30 moles per 100 moles of feed.

Neither of these processes suggest the use of helium as an additive to a stream containing carbon dioxide and methane to raise the critical pressure of the mixture and therefore allow effective distillation of that mixture without carbon dioxide freezeout.

SUMMARY OF THE INVENTION

This invention relates generally to a method for separating acid gases, particularly carbon dioxide, from methane by using cryogenic distillation. Particularly, the process of the invention entails the steps of adding an effective amount of a light gas, preferably helium, to a stream containing methane and carbon dioxide and cryogenically distilling the mixed stream to produce a liquid carbon dioxide stream and an enriched methane stream. The distillation tower or at least a portion thereof may then be operated at a pressure higher than the critical pressure of methane.

The light gas additive may come from a variety of sources. For instance, helium is a natural component of some natural gas streams. Furthermore, helium may be separated from the distilled methane stream by flash or membrane separation means. Thus, the light gas may be recycled and added to the feedstream prior to its introduction into the cryogenic distillation tower.

The process is suitable for methane gas streams containing in excess of 80% carbon dioxide. The process is operable down to very small amounts of carbon dioxide but is most desirably used on feedstreams containing at least 10% carbon dioxide. The feedstream may contain hydrogen sulfide or other acid gases but must be dried prior to introduction into the distillation tower.

The disclosed process may be used on a dried gas stream from a well head or may be used as an add-on process to other physical or chemical processes which are used to separate carbon dioxide and methane.

DESCRIPTION OF THE PREFERRED EMBODIMENTS

As mentioned above, one recurring problem in performing a cryogenic distillation of carbon dioxide and methane lies in the potential of forming carbon dioxide solids in the distillation tower. This problem can be seen in FIG. 1 which is a binary phase diagram of carbon dioxide and methane at 650 psia. This diagram is based on data from Donnelly, H. G. and Katz, D. L., Ind. Eng. Chem. 46,511 (1954). The diagram shows regions of solid carbon dioxide, liquid only, vapor only, vapor and liquid existing together and regions having solids existing with either vapor or liquid.

Figure 1:
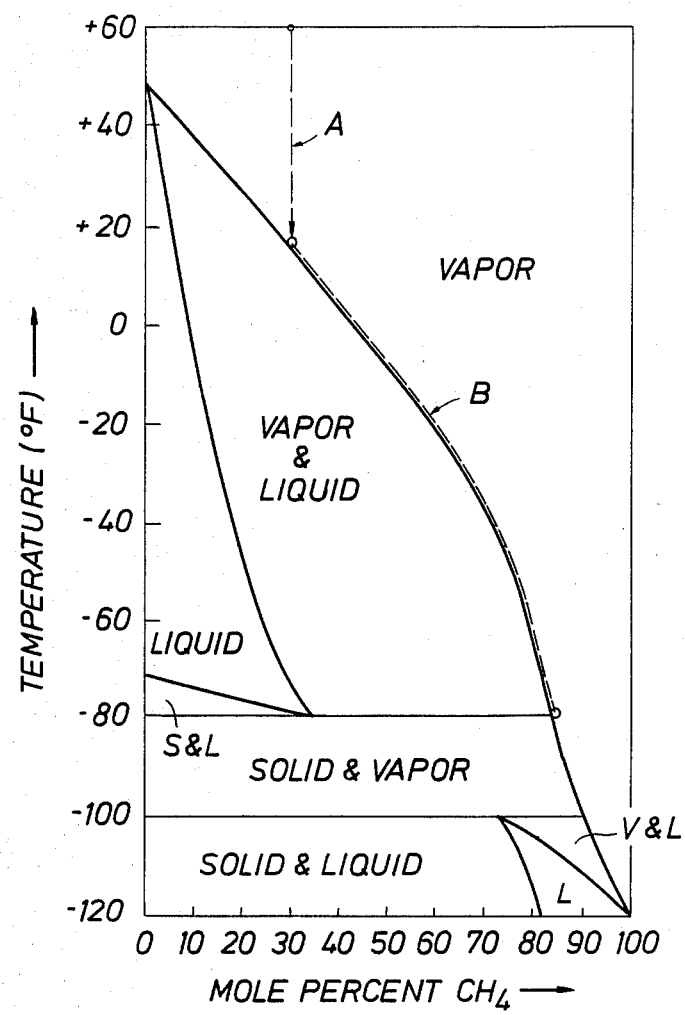
FIG. 1 is a binary phase diagram for methane and carbon dioxide as a function of temperature at 650 psia.

By way of illustration, should one wish to separate a mixture of carbon dioxide and methane at 650 psia, FIG. 1 shows that there is a region of carbon dioxide solids formation which would cause problems. For instance, cooling a 30% methane/70% carbon dioxide mixture initially at 60° F. along line "A" in FIG. 1 will cause liquid to form beginning at about 15° F. At this point, vapor-liquid equilibrium distillation may take place. In the methane enriching section, the vapor, in equilibrium with the liquid, would increase in methane content along line "B". As the temperature is lowered to about −80° F., solid carbon dioxide would begin to form. Further methane enrichment of the vapor products stream cannot be achieved without the formation of solid carbon dioxide. Solid carbon dioxide would render the distillation tower inoperable. Therefore at 650 psia, distillation techniques are limited to this level of separation because of the formation of carbon dioxide solids. The product methane stream in the illustration could have as much as 15% carbon dioxide remaining in it.

Figure 2:
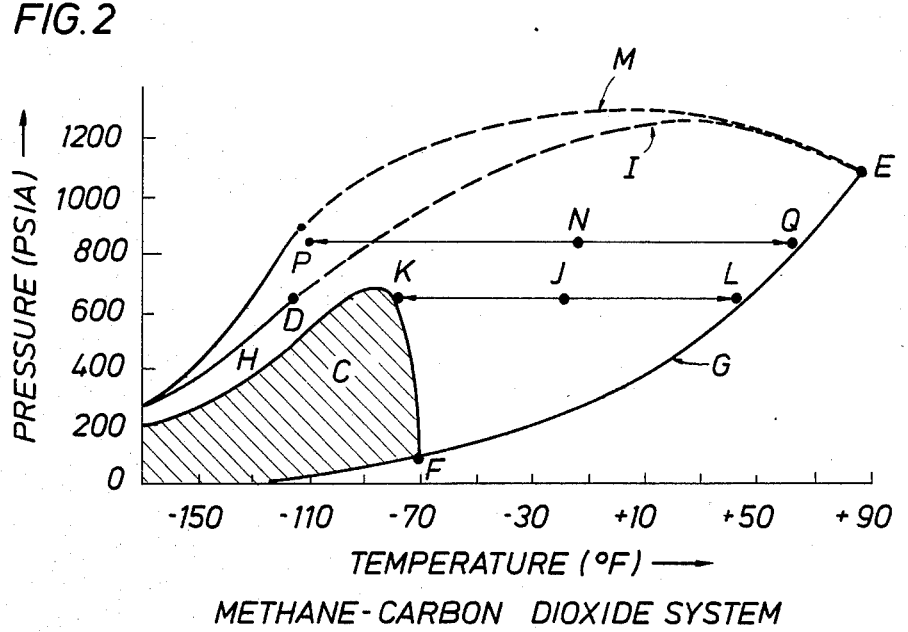
FIG. 2 is a schematic diagram showing the carbon dioxide freezing envelope and critical pressure of gas mixtures, with and without helium, as a function of temperature and pressure.

However, it is possible to avoid the formation of carbon dioxide solids in a cryogenic distillation tower by raising the pressure of the tower. FIG. 2 schematically depicts the carbon dioxide freezing envelope (area "C") on a pressure-temperature phase diagram. On this diagram, the methane critical point is shown at "D" and the carbon dioxide critical point is shown at "E". The carbon dioxide triple point, at which solid, liquid, and gaseous carbon dioxide are in equilibrium, is shown as "F". Curve "G" between points "E" and "F" is the carbon dioxide vapor-liquid equilibrium or vapor pressure line. Curve "H" between point "D" and the graph's pressure ordinate line is the methane vapor pressure line.

Any separation of mixtures containing only methane and carbon dioxide by distillation must take place below the dashed critical pressure line "I" and yet above the carbon dioxide solidification area "C". For instance, methane-carbon dioxide mixture having a composition which places it in FIG. 2 at point "J" may be distilled at about 670 psia to produce two streams having the compositions associated with points "K" and "L". Point "K" represents an enriched methane stream which exists in equilibrium at about −80° F. and 670 psia and would be found at the upper end of the distillation tower. It would be more preferable if the distillation could be carried to lower temperature since the methane content in the overhead product stream would be higher; however, the carbon dioxide solidification region "C" falls in the way at the chosen pressure. One might select a higher pressure to avoid the upper end of area "C", but the critical pressure line "I" then becomes the limiting factor in effecting the separation.

The invention disclosed herein has the effect of raising the critical pressure line "M" of the resulting multicomponent mixture during distillation. Consequently, an equilibrium separation taking place at 800 psia on a multicomponent carbon dioxide-methane-helium mixture beginning at point "N" can result in two product streams characterized by points "P" and "Q" while avoiding the carbon dioxide freezing zone "C". The methane-rich composition at point "P" will have significantly lower carbon dioxide content than does the methane-rich composition at point "K".

It must be emphasized that the graph FIG. 2 is schematic in nature and is included only to show the effect of adding about two to about five molar percent helium to a stream of carbon dioxide and methane for the purpose of improving their cryogenic distillation. Helium is an especially good component for use in this process in that it occurs naturally in natural gas and is reasonably easy to separate from methane.

Figures 3, 3A:
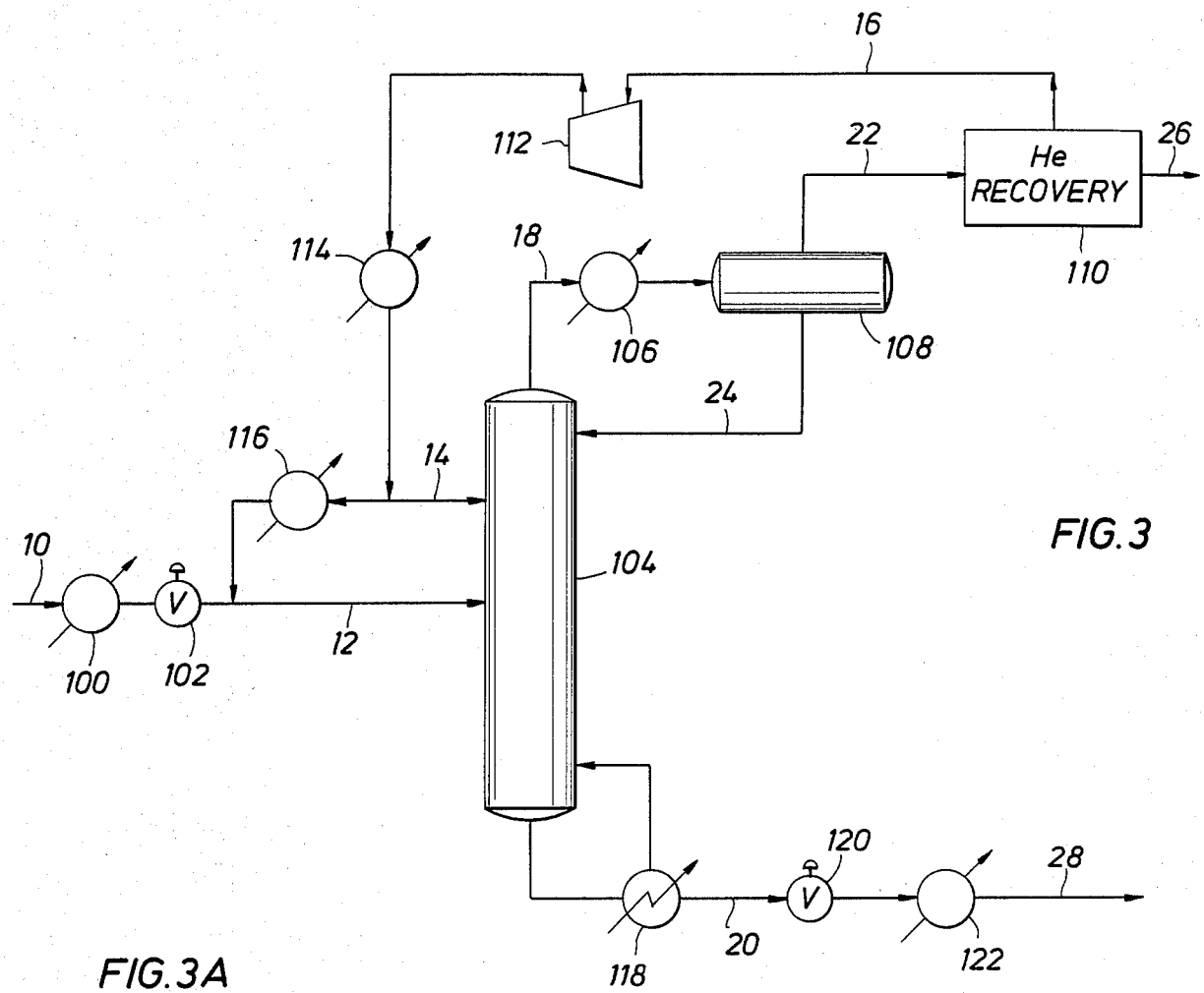
FIG. 3 is a schematic diagram of an example process unit using the present invention.
FIG. 3A is a schematic diagram of a helium recovery process suitable for use with the disclosed process.

FIG. 3 depicts one desirable process exemplifying the concept of separating and recycling helium to aid in the separation of methane and carbon dioxide. TABLE 1 is an approximate material balance showing the temperature and pressure of various streams enumerated in FIG. 3.

TABLE 1

| Stream No. | 10 | 12 | 14 | 16 | 18 | 20 | 22 | 24 | 26 |
|---|---|---|---|---|---|---|---|---|---|
| Temperature (°F.) | 70° | −60° | −100° | −178° | −107° | 55° | −114° | −114° | −120° |
| Pressure (psia) | 1000 | 800 | 800 | 505 | 800 | 800 | 800 | 800 | 505 |
| $CH_4$ (lb-moles/day) | 31,992 | 33,400 | 600 | 2,008 | 113,554 | 1,602 | 32,398 | 81,156 | 30,390 |
| He (lb-moles/day) | 473 | 2,000 | 650 | 2,177 | 4,262 | — | 2,650 | 1,612 | 473 |
| $CO_2$ (lb-moles/day) | 65,997 | 66,000 | — | 3 | 5,363 | 65,047 | 953 | 4,410 | 950 |
| TOTAL | 98,462 | 101,400 | 1,250 | 4,188 | 123,179 | 66,649 | 36,001 | 87,178 | 31,813 |

A dried gas stream from a well head at about 1000 psia containing 67% carbon dioxide, 32.5% methane, and about 0.5% helium is introduced into the unit through line 10. The heat content of this stream is about 328 BTU/SCF. This feedstream may be cooled in an indirect heat exchanger 100 and expanded through Joule-Thompson ("J-T") valve 102. The precooler and J-T valve drop the pressure and temperature to a level suitable for introduction of the stream into the methane-carbon dioxide splitter tower 104. At this point the feedstream is mixed with a helium recycle stream and fed into tower 104. For the purposes of this example, an additional recycle helium stream 14 is fed into the upper portion of the tower.

TABLE 2 is a characterization of the splitter tower 104 made by using an Exxon proprietary computer program.

TABLE 2

Tower Parameter:
Feed Stream No. 12
34,400 lb-moles/D - methane
2,000 lb-moles/D - helium
66,000 lb-moles/D - carbon dioxide
Feed Stream No. 14
600 lb-moles/D - methane
650 lb-moles/D - helium

| | | |
|---|---|---|
| Pressure: | 800 | psia |
| Number of theoretical stages: (including reboiler and condenser) | 20 | |
| Stage of upper feed (No. 14): | 5 | |
| Stage of lower feed (No. 12): | 10 | |
| Reflux Ratio: | 2.42 | |
| Reflux Rate: | 87,178 | lb moles/D |
| Condenser Duty: | −3,100 | kBTU/hr |
| Reboiler Duty: | 9,775 | kBTU/hr |

| Stage No. | T(°F.) | Vapor lb-moles/D | Liquid lb-moles/D | K Methane | K Helium | K Carbon Dioxide |
|---|---|---|---|---|---|---|
| 1 | −113.9 | 36,002 | 87,178 | .966 | 3.983 | .523 |
| 2 | −107.0 | 123,179 | 101,976 | 1.001 | 2.546 | .666 |
| 3 | −103.6 | 137,929 | 87,946 | 1.011 | 2.514 | .671 |
| 4 | −100.4 | 123,948 | 75,049 | 1.024 | 2.860 | .634 |
| 5 | −96.1 | 109,802 | 61,954 | 1.044 | 3.167 | .608 |
| 6 | −91.8 | 96,707 | 41,052 | 1.106 | 4.853 | .488 |
| 7 | −84.6 | 75,805 | 19,762 | 1.422 | 11.450 | .300 |
| 8 | −69.1 | 54,515 | 12,320 | 2.351 | 27.985 | .243 |
| 9 | −58.8 | 47,072 | 12,110 | 2.603 | 30.459 | .273 |
| 10 | −54.0 | 29,161 | 108,718 | 2.465 | 23.985 | .314 |
| 11 | −52.5 | 42,070 | 109,717 | 2.451 | 22.923 | .325 |
| 12 | −50.7 | 43,069 | 109,204 | 2.488 | 23.080 | .332 |
| 13 | −47.2 | 42,556 | 108,415 | 2.577 | 23.428 | .345 |
| 14 | −40.5 | 41,767 | 107,921 | 2.671 | 23.709 | .373 |
| 15 | −28.9 | 41,274 | 108,584 | 2.839 | 23.460 | .428 |
| 16 | −11.5 | 41,937 | 111,472 | 3.038 | 22.070 | .523 |
| 17 | 9.8 | 44,824 | 117,312 | 3.189 | 19.476 | .653 |
| 18 | 29.8 | 50,665 | 124,962 | 3.238 | 16.690 | .784 |
| 19 | 45.0 | 58,315 | 132,444 | 3.211 | 14.520 | .884 |
| 20 | 55.0 | 65,797 | 66,648 | 3.162 | 13.104 | .947 |

The overhead vapor stream 18 from tower 104 is partially condensed in reflux condenser 106. Condenser 106 desirably uses an ethane or ethylene refrigerant. The liquid is accumulated in reflux drum 108 and is returned to the tower as reflux 24. The vapor stream 22 is sent to helium recovery unit 110. Variations of the helium recovery unit 110 are explained in more detail below. Stream 116 is recycled through recycle compressor 112. The various separation processes which may occur in unit 110 require some pressure differential which is made up in compressor 112. The vapor discharged from compressor 112 is heated in exchanger 114 to about −100° F., the stream is split, and a portion 14 is fed directly into tower 104. The remainder is further heated in heat exchanger 116 and mixed with feedstream 10 to form the lower tower feed 12. This upper tower feed 14 places additional helium in the upper portion of the tower where a greater increase in critical pressure is required.

The helium recovery unit produces the desired enriched methane stream 26. The product gas produced in this example yields 965 BTU/SCF. The product may be sent to an LNG plant for liquefaction, if desired, or sent to a pipeline.

Tower 104 utilizes a reboiler 118 operating at about 55° F. to supply heat to the tower.

The liquid carbon dioxide bottoms stream 20 contains any hydrocarbon components, ethane or heavier, as well as most of the other acid gas components which may be found in the feedstream 10. The volatility of hydrogen sulfide relative to methane is quite low; consequently, the hydrogen sulfide content of the product methane will be low and should meet pipeline gas specifications.

The liquid carbon dioxide stream produced by this process is quite versatile. The carbon dioxide may be used for flooding in enhanced oil recovery operations. Alternately, the bottoms stream 20 may be flashed using a J-T valve 120 and used as a refrigerant at various points within the process disclosed above (as symbolized by the heat load in exchanger 122) or as otherwise desired. As an example, flashing stream 20 to 85 psia produces 2,338 kBTU/hr of refrigeration capacity at −64° F.

Figure 4:
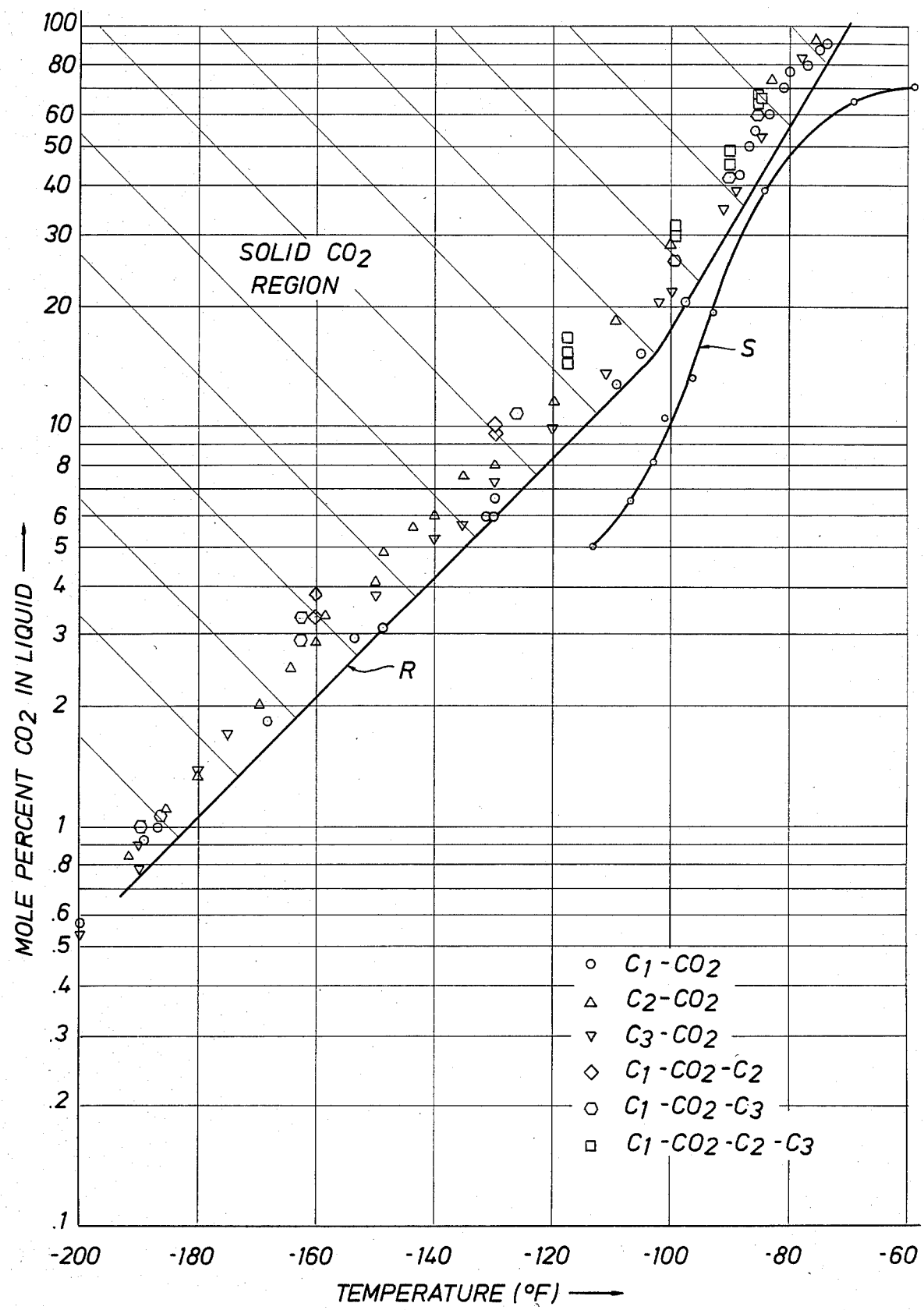
FIG. 4 is a temperature-liquid carbon dioxide fraction diagram showing the operation of the distillation tower exemplified in FIG. 3.

The solubility of carbon dioxide in the liquid phase as a function of temperature is shown in FIG. 4. The operating line ("S") for splitter tower 104 approaches line "R", which conservatively represents the formation of solid carbon dioxide, but does not intersect it. Thus no solid carbon dioxide should be formed in tower 104. The data used to produce line "R" are known from the literature: Cheung, H., Zander, E. H., "Solubility of Carbon Dioxide and Hydrogen Sulfide in Liquid Hydrocarbons at Cryogenic Temperatures," *Chemical Engineering Progress Symposium* Ser. No. 88, Vol. 64, 1968 and Kurata, F., "Solubility of Solid Carbon Dioxide in Pure Light Hydrocarbons and Mixtures of Light Hydrocarbons," GPA Res. Rep. RR-10, February 1974.

As mentioned above, there are several known methods which are useful for separating at least a portion of the helium from stream 22 in helium recovery unit 110. One such method is shown in FIG. 3A. This method utilizes a number of J-T valves to recover a substantial portion of the refrigeration capacity of the stream 22.

Overhead stream 22 is first cooled from −114° F. to about −140° F. in overhead cooler 120. The stream is then flashed to about 570 psia in J-T valve 122 and separated in separator 124. The temperature of separator 124 is about −149° F.

The vapor stream from separator 124 is cooled to −177° F. in secondary cooler 126, flashed to about 545 psia in J-T valve 128, and separated in product separator 130. The temperature of product separator 130 is about −178° F. The vapor product from separator 130 (line 16) is compressed in recycle compressor 112 for subsequent use in splitter tower 104. The helium content of this recycle helium stream is 52 mole percent.

The liquid stream from separator 124 is flashed in J-T valve 132 and mixed with the liquid stream from separator 130 which has been warmed to about −155° F. in heat exchanger 134. The mixed stream is warmed to −120° F. in vaporizer 136. The refrigeration available in exchangers 134 and 136 can be used within the process as desired or as needed elsewhere.

This particular helium separation and recycle method permits use of a relatively small recycle compressor 112 having but a 22.4 Hp driver. Alternative separation processes requiring a higher ΔP such as that discussed below will obviously require a larger capacity compressor.

Other schemes for separating helium from the distillation tower overhead using known flash and distillation techniques are within the scope of one having ordinary skill in this art.

Other types of separation methods such as the membrane separation process disclosed in U.S. Pat. No. 3,239,996 to Huffman et al, issued Mar. 15, 1966, are also suitable although high differential pressures are required. The process is more selective at temperatures above 300° F. Although this process is desirable because of its high helium selectivity, the desirability is somewhat offset by the additional heat exchangers and larger recycle compressor required for effective operation.

The above description and example of the invention are for the purpose of illustration, and it is not intended that the invention be limited except by the scope of the appended claims.

We claim as our invention:

1. A method for separation of a feedstream containing methane and carbon dioxide in a cryogenic distillation tower without producing solid carbon dioxide comprising the steps of:

introducing a diluent stream containing helium into said feedstream to produce a tower feedstream, said helium being introduced in amounts sufficient to raise the critical pressure of the resulting tower feedstream enough to preclude formation of solid carbon dioxide within said tower, and distilling said tower feedstream to produce an enriched carbon dioxide bottoms stream containing a major portion of the carbon dioxide in the feedstream and an enriched methane overhead stream containing substantially all of said helium.

2. The method of claim 1 additionally comprising the steps of separating said overhead stream into a product methane stream and a helium recycle stream and recycling at least a portion of said helium recycle stream as said diluent stream.

3. The method of claim 2 wherein said overhead stream is separated by flashing and cooling.

4. The method of claim 2 wherein said overhead stream is separated by membrane separation means.

5. The method of claim 2 additionally comprising the steps of dividing said helium recycle into at least said diluent stream and another stream and introducing said another stream into the distillation tower at a point above the point at which said tower feedstream is introduced.

6. The method of claim 1 additionally comprising the step of introducing a stream containing helium into said cryogenic distillation tower at a point above the point at which said tower feedstream is introduced.

7. The method of claim 1 wherein at least a portion of said distillation tower is operated at a pressure above the critical pressure of the methane and carbon dioxide contained therein calculated without the inclusion of helium.

8. The process of claim 1 additionally comprising the steps of recovering at least a portion of the refrigeration potential from at least one of the enriched carbon dioxide bottoms stream and the enriched methane overhead stream.

9. The process of claim 1 wherein said feedstream also contains at least one selected from the group consisting of hydrogen sulfide, carbonyl sulfide, carbon disulfide, and mercaptans.

10. A method for the separation of a feedstream containing methane and carbon dioxide in a cryogenic distillation tower without producing solid carbon dioxide comprising the steps of:

cooling said feedstream by heat exchange, expanding said feedstream through expansion means, introducing a diluent stream containing helium to said feedstream in amounts sufficient to raise the critical pressure of the resulting tower feed enough to preclude formation of solid carbon dioxide within said tower, distilling said tower feed in a cryogenic distillation tower wherein at least a portion of said distillation tower is operated at a pressure higher than the critical pressure of the carbon dioxide and methane mixture contained therein calculated without the inclusion of helium to produce a bottoms stream containing a major portion of the carbon dioxide in said feedstream and an overhead stream containing a major portion of the methane in said feedstream, condensing at least a portion of said overhead stream and recycling the condensed overhead stream as reflux in said distillation tower, separating the remaining uncondensed portion of said overhead stream into a helium gas recycle stream and methane product stream, and compressing at least a portion of said helium gas recycle stream for mixing with said feedstream as said diluent stream.

11. The method of claim 10 wherein said helium gas separation step comprises a flash step.

12. The method of claim 10 wherein said helium gas separation step comprises a membrane separation step.

13. The method of claim 10 additionally comprising the step of pretreating said feedstream to remove at least a portion of said carbon dioxide.

14. The method of claim 10 wherein said feedstream also contains hydrogen sulfide.

15. The method of claim 10 additionally comprising the step of introducing a stream containing helium into said cryogenic distillation tower at a point above the point at which said tower feed is introduced.

16. The method of claim 10 additionally comprising the steps of dividing said helium gas recycle stream into at least said diluent stream and another stream and introducing said another stream into the distillation tower at a point above the point at which said tower feed is introduced.

17. The method of claim 10 additionally comprising the step of recovering at least a portion of the refrigeration heat value from at least one of the enriched carbon dioxide bottoms stream and the enriched methane overhead stream.

* * * * *